Figure 1B:
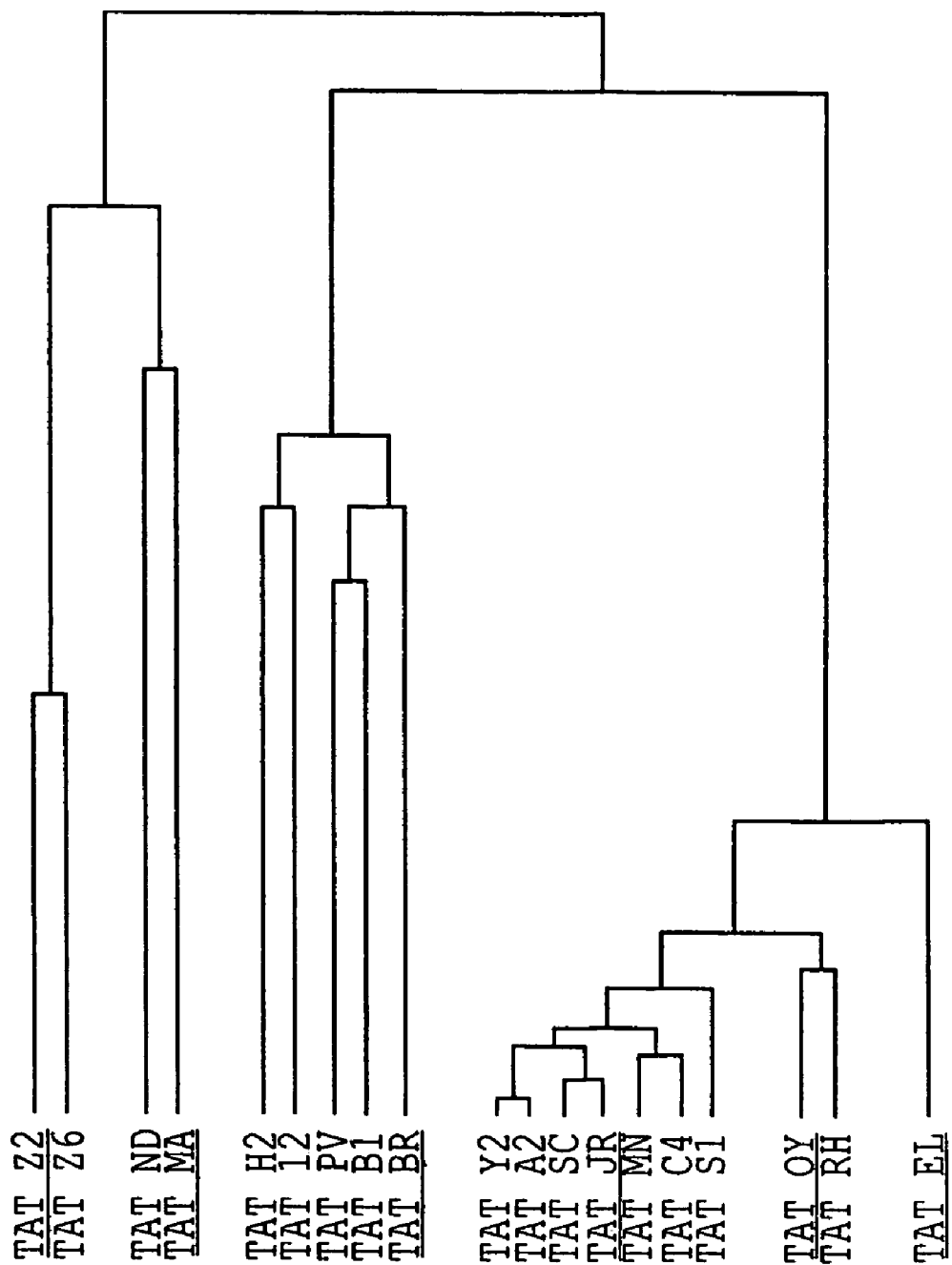
Figure 3D:
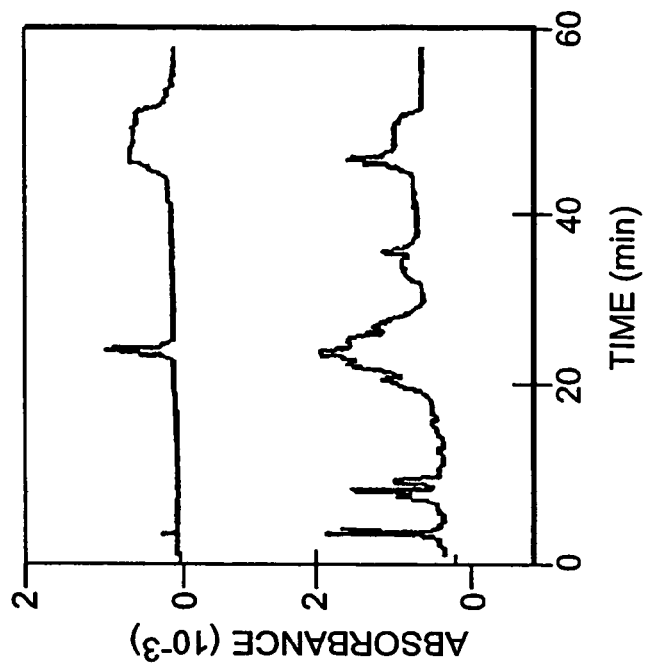
Figure 3C:
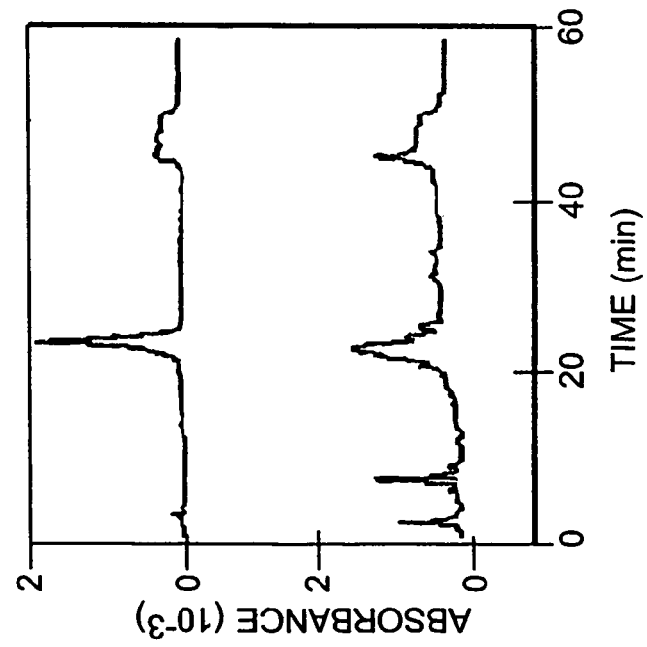
Figure 3F:
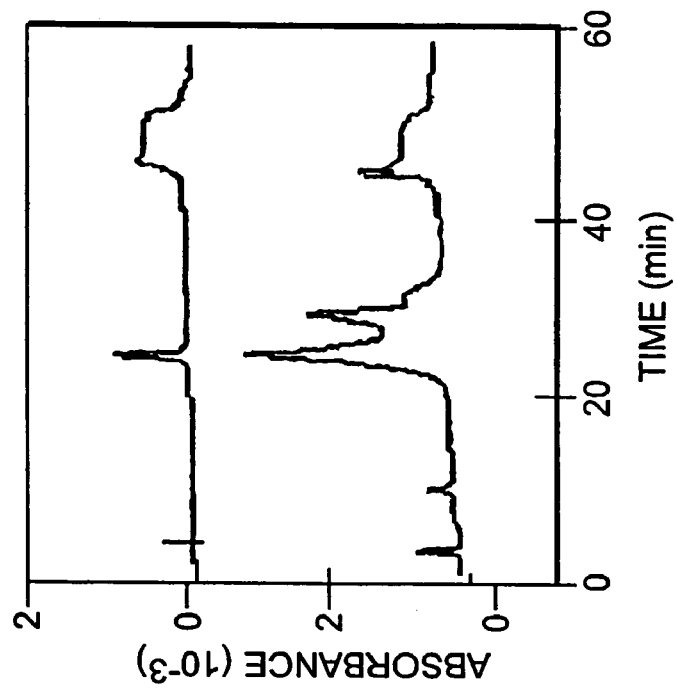
Figure 3E:
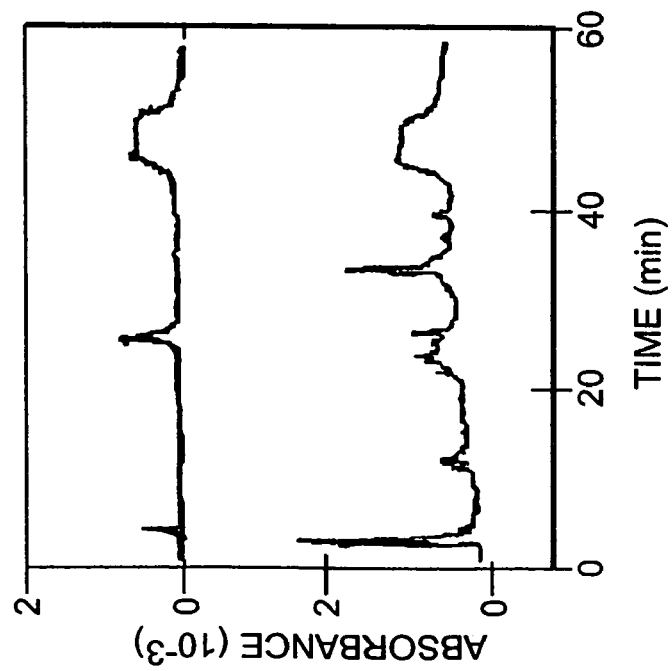
Figure 4B:
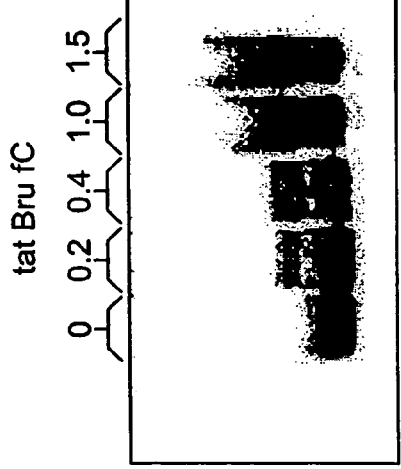
Figure 4A:
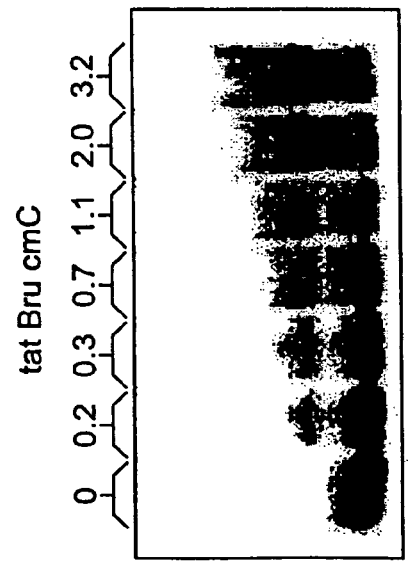
Figure 4D:
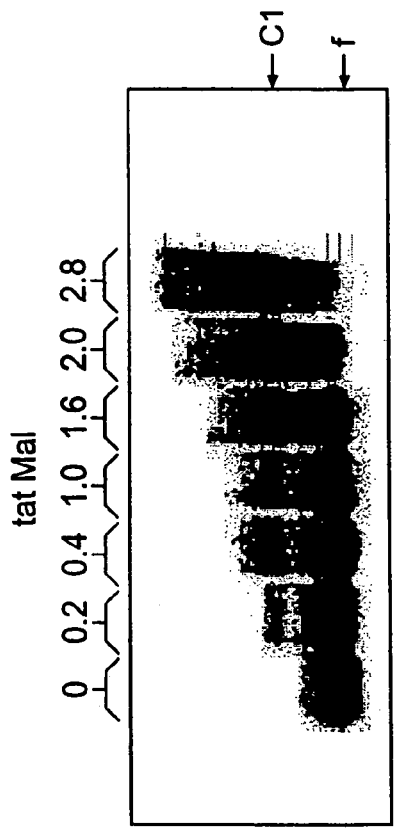
Figure 4C:
Figure 4F:
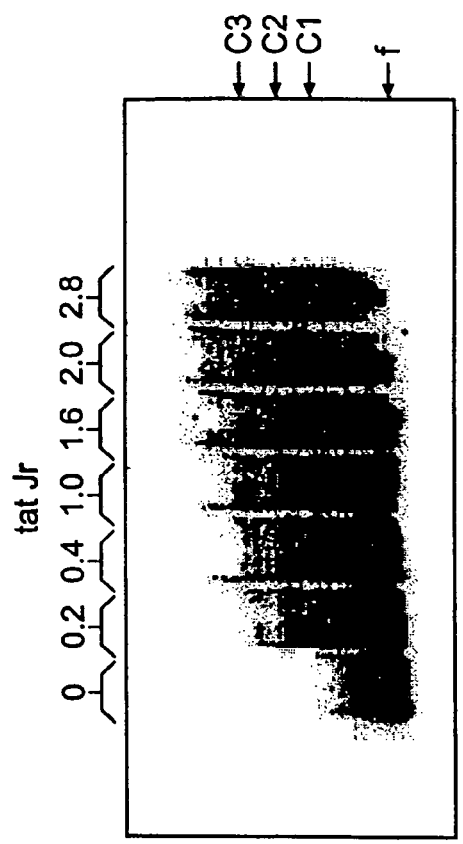
Figure 4E:
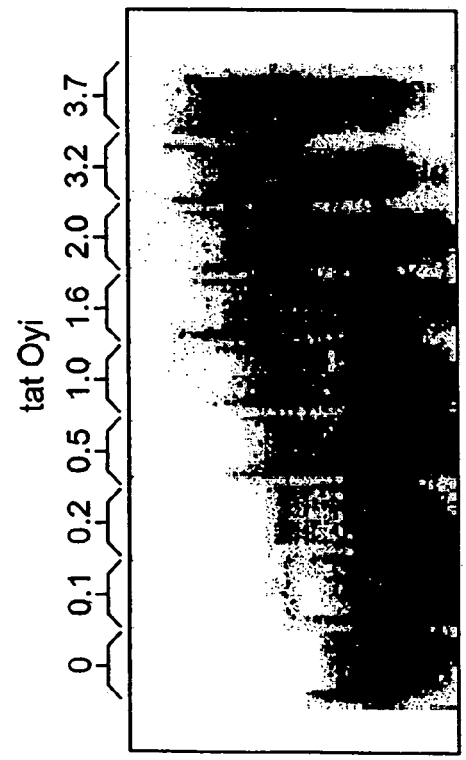
Figure 4G:

US007087377B2

(12) United States Patent
Loret

(10) Patent No.: US 7,087,377 B2
(45) Date of Patent: Aug. 8, 2006

(54) METHOD AND KIT FOR DETECTION OF TAT PROTEIN WITH ANTI-TAT OYI ANTIBODIES

(75) Inventor: Erwann Loret, Marseilles (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/969,191

(22) Filed: Oct. 21, 2004

(65) Prior Publication Data

US 2005/0106161 A1 May 19, 2005

Related U.S. Application Data

(62) Division of application No. 09/958,654, filed as application No. PCT/FR00/00938 on Apr. 12, 2000, now abandoned.

(30) Foreign Application Priority Data

Apr. 13, 1999 (FR) .................................. 99 04610
Dec. 29, 1999 (FR) .................................. 99 16633

(51) Int. Cl.
*C12Q 1/70* (2006.01)

(52) U.S. Cl. ............................ 435/5; 435/7.1; 435/7.9; 435/7.92; 435/974; 435/975; 435/962; 530/388.3; 530/389.4

(58) Field of Classification Search .................... 435/5, 435/7.1, 7.9, 7.92, 974, 975, 962; 530/388.3, 530/389.4
See application file for complete search history.

(56) References Cited

U.S. PATENT DOCUMENTS 4,281,061 A * 7/1981 Zuk et al. .................... 435/7.9
5,019,510 A 5/1991 Wain-Hobson et al.
5,132,205 A * 7/1992 Pronovost et al. ............. 435/5
5,889,175 A 3/1999 Mehtali ................... 536/23.72
5,891,994 A 4/1999 Goldstein ................... 530/329

FOREIGN PATENT DOCUMENTS

DE 195 14 089 A1 10/1986

OTHER PUBLICATIONS

Harlow et al. Antibodies: A Laboratory Manual. N.Y., Cold Spring Harbor, 1988. pp. 558-559. QR186.7.A53.*
Brake DA, et al., Characterization of Murine Monoclonal Antibodies to the TAT Protein from Human Immunodeficiency Virus Type 1. J. Virol., vol. 64, pp. 962-965 (1990).
Buanec, HL, et al., A prophylactic and therapeutic AIDS vaccine containing as a component the innocuous Tat toxoid. Biomed & Pharmacother., vol. 52, pp. 431-435 (1998).
Caselli E., et al., DNA immunization with HIV-1 *tat* mutated in the *trans* activation domain induces humoral and cellular immune responses against wild-type Tat. J. Immunol., vol. 162, pp. 5631-5638 (1999).
Goldstein, g. HIV-1 Tat protein as a potential AIDS vaccine. Nature Medicine, vol. 2, pp. 960-964 (1996).
Gregoire CJ and Loret EP, Conformational heterogeneity in two regions of TAT results in structural variations of this protein as a function of HIV-1 isolates. J. Biol. Chem., vol. 271, pp. 22641-22646 (1996).
Huet, T. et al., A highly defective HIV-1 strain isolated from a healthy Gabonese individual presenting an atypical Western blot. AIDS, vol. 3, pp. 707-715 (1989).
Lefevre, EA. et al. Cutting edge: HIV-1 Tat protein differentially modulates the B cell response of naive, memory, and germinal center B cells. J. Immunology, vol. 163, pp. 1119-1122 (1999).
Pèloponèse, J-M. et al., Full peptide synthesis, purification, and characterization of six Tat variants. J. Biol. Chem., vol. 274, pp. 11473-11478 (1999).
Re, MC, et al., Effect of antibody of HIV-1 tat protein on viral relication *in vitro* and progression of HIV-1 disease *in vivo*. J. Acquired Immune Deficiency Syndromes and Human Retrovirology, vol. 10, pp. 408-416 (1995).
Internation Search Report for Application PCT/FR 00/00938 (2000).
French Search Report for Application FA 582024 and FR 9916633 (2000).
Hungarian Search Report for Application P0200841 (2002).
Riffkin et al. "A single amino-acid change between the antigenetically different extracellular serine proteases V2 and B2 from Dichelobacter nodosus", Gene, vol. 167 (1995), pp. 279-283.
Abaza et al. "Effects of amino acid substitutions outside an antigenic site on protein biding to monoclonal antibodies of predetermined specificity obtained by peptide immunization", J. Prot. Chem., vol. 11, No. 5 (1992), pp. 433-444.
Cruse et al., Illustrated Dictionary of Immunology (Boca Raton, FL, CRC Press, Inc., 1995), p. 309.
Paul, Fundamental Immunology, (Philadephia & New York, Lippincott-Raven Publ., 1993), pp. 250 and 1311-1312.
Cohen et al., "Pronounced acute immunosuppression in vivo mediated by HIV Tat challenge", Proc. Nat'l Acad. Sci. USA, vol. 96, No. 19 (1999) pp. 10842-10847.

* cited by examiner

*Primary Examiner*—Jeffrey Stucker
(74) *Attorney, Agent, or Firm*—Finnegan, Henderson, Farabow, Garrett & Dunner LLP

(57) ABSTRACT

The invention relates to an anti HIV 1 vaccine comprising the entire or part of the Tat HIV 1 protein, in addition to the identification of said protein in individuals affected by HIV. The Tat protein is a protein of the HIV 1 Oyi variant.

2 Claims, 12 Drawing Sheets

FIG. 1A

H-Met-Glu-Pro-Val-Asp-Pro-Arg-Leu-Glu-Pro-Trp-Lys-His-Pro-
Gly-Ser-Gln-Pro-Lys-Thr-Ala-Ser-Asn-Asn-Cys-Tyr-Cys-Lys-
Arg-Cys-Cys-Leu-His-Cys-Gln-Val-Cys-Phe-Thr-Lys-Lys-Gly-
Leu-Gly-Ile-Ser-Tyr-Gly-Arg-Lys-Lys-Arg-Arg-Gln-Arg-Arg-
Arg-Ala-Pro-Gln-Asp-Ser-Lys-Thr-His-Gln-Val-Ser-Leu-Ser-
Lys-Gln-Pro-Ala-Ser-Gln-Pro-Arg-Gly-Asp-Pro-Thr-Gly-Pro-
Lys-Glu-Ser-Lys-Lys-Lys-Val-Glu-Arg-Glu-Thr-Glu-Thr-Asp-
Pro-Glu-Asp-OH   (SEQ ID NO:20)

FIG. 2

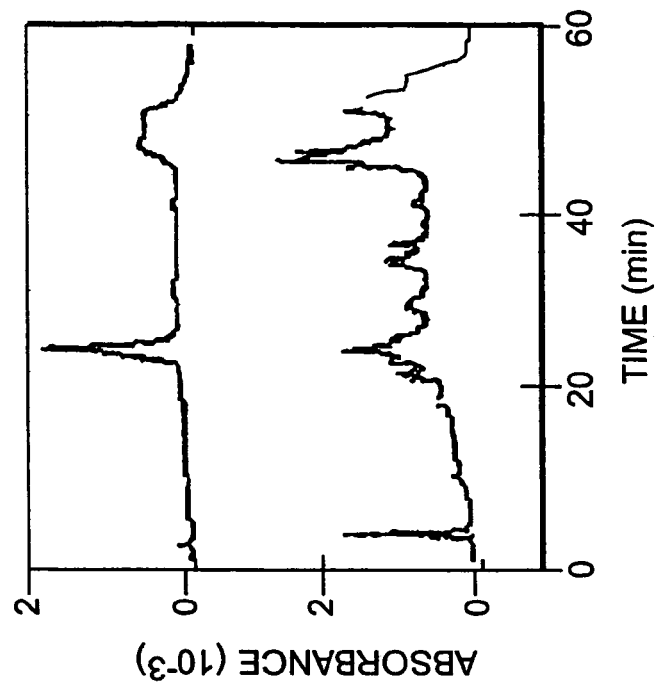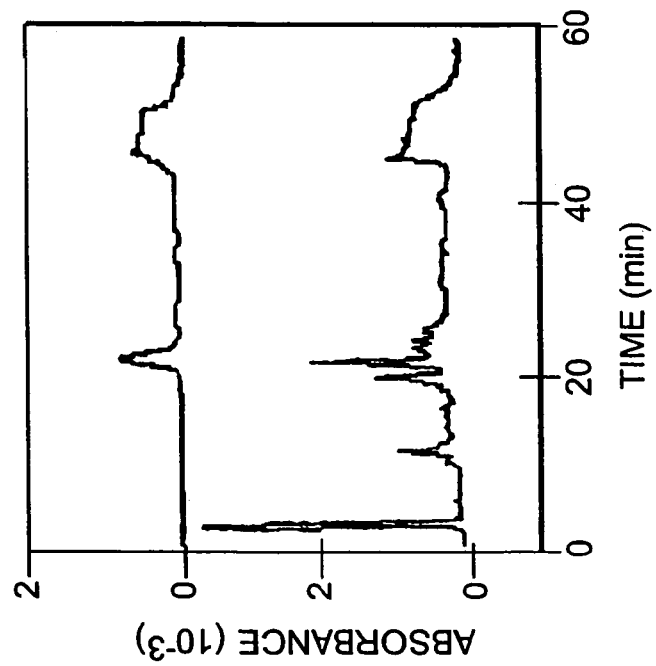

| tat | Kd (µM) |
|---|---|
| Bru | 0.070 |
| rC | 0.081 |
| cmC | 0.145 |
| Oyi | 0.132 |
| Jr | 0.052 |
| Mal | 0.131 |
| Z2 | 0.054 |
| Eli | |

METHOD AND KIT FOR DETECTION OF TAT PROTEIN WITH ANTI-TAT OYI ANTIBODIES

This is a division of application Ser. No. 09/958,654, now abandoned, which has a 35 U.S.C. §371 date of Feb. 6, 2002, and is the U.S. National Phase of International application PCT/FR00/00938, filed Apr. 12, 2000, which claims priority to French applications 99/04610, filed Apr. 13, 1999, and 99/16633, filed Dec. 29, 1999, all of which are incorporated herein by reference.

The subject of the present invention is an anti-HIV-1 vaccine comprising all or part of the HIV-1 Tat protein and the preparation of monoclonal or polyclonal antibodies capable of recognizing several Tat variants and a method for detecting Tat in a biological sample.

The subject of the present invention relates to the use of regulatory protein of the human immunodefiency virus (HIV), the Tat protein, as a vaccine against this virus and the detection of this protein in individuals infected with HIV.

Tat is a viral protein which is essential for the expression of the viral genes and the replication of the HIV-1 virus. The Tat gene is composed of two exons encoding a protein of 99 to 106 residues depending on the isolates. However, a Tat activity with forms containing 86 residues having a portion of the C-terminal end which has been deleted has already been described. These Tat derivatives with 86 residues are thought to be laboratory artifacts or ancestral forms which no longer exist in the natural state. This protein allows the activation of the HIV-1 genes by virtue of its attachment to a nucleotide target called TAR located at the 5' end of the HIV-1 mRNAs. It is secreted by cells infected with HIV and is essential for an effective reverse transcription of HIV-1. Once outside the cell, it is capable of activating distant infected cells and of inducing the immunodeficiency of noninfected T cells. In addition, it is directly involved in AIDS-related pathological conditions such as Kaposi's sarcoma.

The development of the vaccine against AIDS is highly anticipated by the whole planet, but the production of a vaccine against AIDS has two major difficulties. The first is linked to the extreme variability of the envelope protein GP120. The second difficulty is due to the fact that the anti-GP120 antibodies appear to aggravate the disease for patients with declared AIDS. However, preliminary results indicate that a protective effect could be possible with anti-GP120 antibodies in people who have not been previously contaminated. A phase II with an anti-GP120 vaccine has been initiated by the company Roche in the United States. The cohorts selected for this phase II are well monitored from the medical point of view. It will however be difficult to obtain an equivalent medical supervision when the vaccine is marketed.

With GP120, Tat is detected in the blood of patients infected with HIV-1. The activity of the macrophages and the cytotoxic T lymphocytes (CTL) responsible for eliminating all the cells infected with a virus is gradually blocked by Tat, which therefore acts as an immunosuppressant. Anti-Tat antibodies (or active ingredients targeting Tat) should allow the restoration of the activity of the CTLs and of the macrophages.

Tat is therefore a favored target both for the development of anti-Tat antivirals and for a vaccine approach.

The Tat protein has therefore been the subject of experiments. Preclinical trials, obtained with a biologically inactive recombinant Tat protein (Tat toxoid), have shown in particular that Tat toxoid causes, in seronegative patients, a high and persistant production of anti-Tat antibodies (Le Buanec et al., 1998). In seropositive and immunodeficient patients, a significant increase in the anti-Tat antibody level is observed compared with the normal anti-Tat antibody level (Westendorp et al., 1995).

This Tat toxoid is a recombinant protein, which is made biologically inactive after carboxymethylation of the Tat cysteines. A carboxymethylated Tat (Tat Bru cmC) has also been produced, which has a loss of the transactivation activity even though the same Tat variant with the free cysteines (Tat Bru fC) is capable of transactivating. Tat Bru cmC is capable of binding to TAR with a comparable affinity to Tat Bru fC.

A major disadvantage in the use of carboxymethylated Tat as a vaccine is that the chemical modification of the cysteines causes conformational changes that have been observed by circular dichroism and NMR. Although conformational changes exist among the various Tat variants, carboxymethylation of the cysteines causes major modifications in the folding of the peptide chain of Tat which, as a result, is not a good candidate for the preparation of an anti-Tat vaccine.

It is therefore advisable to use, in an anti-HIV-1 vaccine, a Tat protein which is defective but which possesses structural characteristics similar to the functional Tats. This Tat should indeed have a three-dimensional structure which is as close to the natural Tat proteins as possible so as to be capable of inducing a similar immune response to that induced by the natural Tats, but which cannot transactivate, that is to say, as indicated above, incapable of activating distant infected cells and of inducing the immunodeficiency of noninfected T cells. It is indeed crucial to inhibit this immunodeficiency.

The subject of the present invention is therefore an anti-HIV-1 vaccine comprising all or part of at least one HIV-1 Tat protein capable of binding to TAR and incapable of transactivating, in combination with a pharmaceutically acceptable vehicle and, where appropriate, one or more appropriate immunity adjuvants. This Tat protein should be capable of generating, in an animal to which this protein might be administered, a production of antibodies capable of recognizing other variants of this protein and in a level which is sufficient to inhibit the transactivation of the said variants.

Thus, not only can a Tat protein be used for the preparation of a vaccine in accordance with the invention, but also only one or more portions of this protein capable of fulfilling the functions desired for the Tat protein in the context of the present invention. The abovementioned vaccine may also comprise a combination of various Tat proteins or the portions of various Tat proteins.

According to an advantageous embodiment of the invention, when the Tat protein is used in its entirety, it preferably comprises from 99 to 106 amino acids, and more preferably still 101 amino acids.

The expression "part of the Tat protein" is understood to mean any fragment or combination of fragments of one or more Tat proteins belonging or otherwise to the same variant, which is sufficiently immunogenic to give rise to a production of antibodies. Preferably, the said fragment comprises between 15 and 30 amino acids, preferably between 18 and 25 amino acids. This definition is valid every time that this expression is used in the present application.

The Tat protein which can be used in the vaccine in accordance with the invention should therefore be different from the functional Tat proteins which are termed as "natural", that is to say which are extracted from various HIV-1 strains present in the natural state, so as to be incapable of transactivating while binding to TAR. That is the reason why the Tat used in the vaccine in accordance with the invention have a nucleotide sequence having at least one mutation compared with the nucleotide sequence of a functional Tat. This mutation, which is generally a point mutation, may for example give rise to the suppression, the addition or substitution of one or more amino acids.

The Tat variant corresponding to the Bru isolate (86 residues) was studied and five other variants each representative of the structural diversity observed with this protein (Grégoire et Loret, 1996): Tat Z2 (86 residues), Tat Mal (87 residues), Tat Eli (99 residues), Tat Oyi (101 residues) and Tat Jr (101 residues) were synthesized. Six structural groups among all the HIV-1 isolates have thus been determined according to the size of the proteins and the nature of their mutations. It was probable that all these variants had similar pharmacological activities to Tat Bru, which has been synthesized twice, with the carboxymethylated cysteines (Tat Bru cmC) and then with the free cysteines (Tat Bru fC). The chemistry used was of the fastFmoc type with the HBTU activator. The purification of the proteins was carried out by high-performance liquid chromatography. It has been found that all these synthetic proteins are capable of binding to TAR, but large disparities have been observed in the transactivation test of HeLa cell. The most surprising result was the absence of transactivation observed with the Tat Oyi variant. There was also no transactivation observed with the Tat Bru derivative possessing the carboxymethylated cysteines. The aqueous phase circular dichroism (CD) study on these synthetic proteins indeed shows that the chemical modification of Tat Bru cmC significantly modified the structure of Tat Bru. On the other hand, Tat Oyi has a similar structure to the others as attested by its CD spectrum.

The HIV-1 Oyi strain was identified in a Gabonese patient (more precisely a pregnant woman) in 1988 (Huet et al., 1989). This patient was perfectly healthy although she had been seropositive for several years. Apparently, the fact that a defective Tat protein was present in this HIV-1 strain prevented the progression to AIDS in this patient and conferred immunity on her against the AIDS virus. Indeed, the epidemiological studies carried out in the field have shown that the patients infected with HIV-1 Oyi were long-term nonprogressors.

The HIV Oyi strain belongs to subtype B corresponding to the HIV-1 strains which are the most widespread in Europe and in North America. The Gabonese woman in whom the HIV Oyi strain was identified belonged to a group of 31 people located in the rural province of Haut Ogooué in the south east of Gabon. This group was identified in 1986 during a seroepidemiological analysis carried out on approximately 2000 people infected in the whole of Gabon. This Haut Ogooué group had attracted attention because the people infected were in good health and also exhibited a completely atypical Western blot profile. Indeed, it was not possible to detect, in these people, the presence of anti-gp 120, anti-gp 160 and anti-gp 41 antibodies whereas anti-gag and anti-pol antibodies were identified (Huet et al., 1989).

A group of 750 pregnant women from this same Haut Ogooué province were then studied and showed that 25 of them (that is 3.3%) were HIV positive by the ELISA test. Among these 25 women, 23 had an atypical Western blot profile characteristic of the region (see above). About 10 of the women were followed for 2 years including the one possessing the HIV-1 Oyi strain.

During this period, the atypical serological profile remained constant, excluding the possibility of a recent infection which would not have allowed time for the formation of anti-gp120 antibodies. The presence of a HIV-2 infection was excluded because there was no reaction to HIV-2 gag and only 2 cases of HIV-2 infection had been reported in Gabon, located in a coastal region. All the patients monitored remained in good health with no loss of weight or opportunistic disease during the 2 years of the study (Huet et al., 1989).

The woman identified Oyi was of rural origin, in good health and seronegative for HTLV-1 and HIV-2. The coculture of her lymphocytes with PPMCs revealed an RT activity only after 15 days, which is very unusual. The virus also had a nearly undetectable cytopathic activity. Although the culture supernatant allowed the infection of PBMC, practically no replication was possible on normal lymphocytic lines such as H-9 and CEM or U-937 monocytes. To validate this analysis, similar results were observed with 17 other patients of the same region, confirming the absence of anti-gp 120 antibodies in all the cases. It is of interest to note that the serum of a normal HIV-1 donor is capable of recognizing the HIV-1 Oyi gp 120 (Huet et al., 1989). The HIV-1 Oyi virus was therefore cloned; sequencing revealed no fault except for the Tat gene (Huet et al., 1989).

The mutation of Cys 22 to Ser appears to be the reason for the loss of transactivation and the reversion of this mutation makes it possible to restore the Tat activity.

Moreover, it was observed that in the absence of Tat, the reproduction of the virus is possible but at a very low level. There is therefore a close relationship between the virulence of HIV and the Tat transactivation efficiency. This epidemiological study shows once again the close relationship which exists between the mortality from this disease and the rate of replication of HIV. Tat therefore appears to allow HIV to reach the rate of replication which changes this viral infection to a deadly disease.

Furthermore, this study of these atypical patients of the Haut Ogooué region revealed the protection which the defective HIV strains would appear to provide compared with the normal HIV strains. Indeed, PCR analysis of lymphocytes freshly collected from several atypical patients are thought to have revealed the presence of normal HIV strains. The protective mechanism does not involve anti-gp 120 antibodies, the latter being absent from these patients. The action of the cytotoxic T lymphocytes could be the mechanism which allowed the eradication of the virus.

A relatively recent epidemiological study carried out in Gabon (Delaporte et al., 1996) indicates a low percentage of people infected with HIV (2 to 3%) compared with other African countries. The Oyi subtype appears to have completely disappeared from the population and the Gabonese woman from whom the HIV-1 Oyi strain was taken was in perfect health in 1995 and had given birth to 3 children who were all seronegative. The HIV-1 Oyi virus was no longer detectable in her.

The Tat protein of the HIV-1 Oyi variant, therefore, appears to be the best candidate for entering into the composition of an anti-HIV-1 vaccine. However, an inactivated Tat is not necessarily immunogenic. Now, the whole benefit of a vaccine is to generate the production of antibodies, and what is more, in the present case, of antibodies that are active against other Tat variants. Surprisingly, the invention demonstrates this. The vaccine in accordance with the invention, therefore, comprises, according to a particularly advantageous embodiment, the Tat, as a whole or in part, of the HIV-1 Oyi variant.

The advantages of an anti-Tat vaccine may even be envisaged at several levels. In asymptomatic patients, it would be possible to delay the progression toward AIDS by limiting the immunodeficiency. Such a vaccine could allow the patient to retain an effective immunity against the virus, as appears to be the case at the onset of the infection. In particular, the restoration of the activity of the cytotoxic T lymphocytes (CTL) and of the macrophages, which are not infected by HIV but whose activity is inhibited by Tat, would have the consequence of allowing the patients to become nonprogressors.

In patients with declared AIDS, an anti-Tat vaccine could limit the incidence of certain pathological conditions such as Kaposi's sarcoma or neurological syndromes which appear to be linked to a direct action of the Tat protein following their secretion by HIV-infected cells.

The benefit of the HIV-1 Oyi variant in the context of the present invention is moreover confirmed by Western blot experiments (gel photographs not shown in the present application) and the Elisa test carried out by the inventors in order to determine if there was cross recognition between the different Tat variants.

Indeed, in these two types of experiment, three different anti-Tat sera were tested against seven Tat variants.

Rabbits were immunized with Tat Oyi, Tat Bru cmC and Tat Eli according to a conventional immunization protocol in the presence of Freund's adjuvant. The polyclonal sera obtained after 53 days were analyzed by Western blotting and an Elisa test. The titers observed are, respectively, 700, 11 and 660 pM for the anti-Oyi, anti-Bru cmC and anti-Eli antibodies.

Under denaturing conditions, the Western blot experiments show that the anti-Tat Oyi serum and the anti-Tat Eli serum are incapable of showing cross immunogenicity with all the variants as is the case with the anti-Tat Bru cmC serum.

Tat Bru cmC is a variant whose cysteines are carboxymethylated. This chemical modification of the cysteines not only causes the loss of transactivation activity (Péloponèse et al., 1999) but also the loss of the 3D structure of this variant which converts to a random coil (unpublished result). It is not therefore surprising to observe that the anti-Tat Bru cmC serum is capable of recognizing all the variants when they are denatured.

Under nondenaturing conditions, the Elisa test (FIG. 7) shows that the anti-Tat Oyi serum is capable of recognizing all the variants like the anti-Tat Bru cmC serum. On the other hand, the anti-Tat Eli serum is still incapable of recognizing all the variants. It therefore appears that conserved 3D epitopes exist in numerous Tat variants. However, only the specific immunogenic character of Tat Oyi makes it possible to generate these antibodies in a large quantity. There is therefore a high probability for the presence of Tat in patients to have been underestimated up until now. The dilution of the three sera is 1/1000. In the same experiment, but without dilution, the anti-Tat Eli serum can also recognize all the other Tat variants. It is advantageous to note that the acetylation of lysin 50 of Tat Bru (Tat Bru K50) allows recognition by the anti-Tat Eli serum in a low concentration.

These experiments carried out with these three rabbit polyclonal sera, therefore, confirm the benefit of Tat Oyi as a vaccine. Furthermore, the anti-Tat Oyi serum is capable of inhibiting transactivation on HeLa cells with Tat Bru or Tat Eli. The anti-Tat Eli serum used as a control shows that the production of antibodies from even an active variant does not ensure cross recognition of all the Tat variants as is observed with Tat Oyi. Tat Oyi, which is a long variant (101 residues), allows better recognition of the Tat variants compared with Tat Bru cmC which is a short variant (86 residues). The HIV-1 strains with short Tat variants have practically disappeared and appear to have been laboratory artifacts (Jeang et al., 1999). Furthermore, the anti-Tat Oyi serum exhibits high specificity since it no longer recognizes the denatured forms (or linear epitopes) of the Tat variants. Conversely, there is a significant risk for the anti-Tat Bru cmC serum to generate autoimmune antibodies in human beings because of the high structural diversity of Tat Bru cmC. Antibodies capable of recognizing human albumin existed in the anti-Tat Bru cmC serum (data not shown).

The preservation of the three-dimensional structure of at least one Tat epitope is therefore essential for the recognition of other Tat variants by the anti-Tat 3D antibodies.

Moreover, it was shown that the anti-Tat Oyi antibodies were capable of inhibiting the transactivation of the Tat Eli proteins.

The subject of the present invention is therefore also a method for preparing anti-Tat monoclonal or polyclonal antibodies capable of recognizing several Tat variants. Indeed, it should be emphasized that these antibodies can therefore be used to detect, in individuals who may have been infected with HIV, the presence of the Tat protein in their blood regardless of the variant.

The present invention therefore relates to a method for preparing anti-Tat polyclonal antibodies capable of recognizing several Tat variants, comprising:

- the immunization of an animal by means of a Tat protein or part of this Tat protein combined with an immune response adjuvant,
- the purification of the specific antibodies contained in the serum of the immunized animals.

The immunization of the animal may be carried out by any mode of introducing the Tat protein or part of this Tat protein into this animal such as: injection, inhalation, oral administration, subcutaneous intradermal, intraperitoneal, intravenous or intramuscular.

The immunization of the animal may also be carried out by means of an in vivo and in situ expression of a vector not only carrying the sequence of the Tat protein as a whole or in part but also all the system necessary for the expression of the Tat protein according to techniques well known to a person skilled in the art.

The purification of the specific antibodies contained in the serum of the immunized animals may, for example, be carried out on an affinity column to which the protein or part of the protein which served as antigen has been attached beforehand.

According to an advantageous embodiment of the present invention, the Tat protein or part of the Tat protein used in the immunization step of the above-mentioned method corresponds to the Oyi variant or to the Bru cmC variant.

According to another embodiment of the present invention, the abovementioned protein is a chemically synthesized protein.

The position of seven cysteine residues (region 22–37) is highly conserved among all the Tat variants and the importance of 6 of these cysteine residues for the transactivation is widely described in the literature (Jeang, 1996).

Consequently, it is entirely possible to envisage mutating a Tat variant on at least one of these cysteines in order to render the said variant incapable of transactivating while having the desired properties in the context of the present invention. This mutation may, for example, consist in a substitution of the cysteine for another amino acid such as a serin or an alanin.

A target region, which ought to be conserved in the Tat variants, has been identified from the 3D structure of Tat Bru by heteronuclear 2D NMR. This target partly consists of the N-terminal region and the basic region of the Tat sequence.

The 3D structure of the Tat Bru variant shows that the region rich in cysteines is close to the three-dimensional space of the N-terminal region and of the basic region. This indicates that the carboxymethylation of the cysteines probably modifies the structure of this target and confirms the fact that the Tat thus modified cannot be considered as a potential candidate for the preparation of an anti-HIV vaccine.

Moreover, solid phase chemical synthesis of the various Tat proteins has been done. At the current level of knowledge in the field, the advantages presented by this mode of synthesis consist in the lower costs of production, the better yields compared with the Tat produced by molecular biology and the absence of contaminations.

Thus, advantageously, the Tat used in the vaccine in accordance with the invention is prepared by chemical synthesis and more particularly by solid phase chemical synthesis, such as a synthesis of the FMOC, and preferably fastFMOC, type. A method of synthesis using protective groups of this type is also a subject of the present invention.

However, the Tat used in the vaccine in accordance with the invention may also be synthesized in any other way, for example by means of recombinant techniques well known to a person skilled in the art. These cloning and expression systems used in the context of these techniques may be derived from microorganisms such as *Escherichia coli, Bacillus, Streptomyces* and *Saccharomyces* but also from yeast, insect and mammalia cells. The Baculovirus expression systems may also be envisaged. Quite obviously, the vectors carrying the sequence of the Tat protein as a whole or in part will comprise all the expression system necessary to do this, according to techniques well known to a person skilled in the art.

Furthermore, in order to avoid any potential risk of toxicity because of the passage of the Tat protein, in particular Tat Oyi, into the membranes, it would be advisable to modify the sequence Arg-Gly-Asp present at the C-terminus of the sequence of all the Tat variants. This sequence is indeed essential for the membrane passage because it recognizes a membrane receptor at the surface of the cells (Jeang, 1996). More particularly, this modification may consist of the substitution of this sequence by the sequence Lys-Ala-Glu which would have no influence on the structure, or possibly the sequence Ala-Ala-Ala.

As indicated above, it is highly probable that the number of people infected with HIV has been underestimated up until now because of the failure to detect in them, for example in their blood, the presence of the Tat protein. The benefit of the present invention is to provide means for detecting the largest possible number of Tat variants by means of a limited number of antibodies.

The subject of the invention is therefore also a method for detecting the presence of the Tat protein or of part of the Tat protein in a biological sample, comprising:
bringing said sample into contact with anti-Tat antibodies capable of giving rise to antigen-antibody complexes with several Tat variants,
determining the presence of the antigen-antibody complexes.

The expression "anti-Tat antibody" is understood to mean not only whole antibodies but also fragments of antibodies or chimeric antibodies capable of fulfilling the desired role in the context of the present invention, namely recognizing all or part of the Tat protein.

The determination of the presence of the antigen-antibody complexes is carried out by methods well known to a person skilled in the art. In particular, the reagents allowing the detection of these complexes may carry a marker or may be capable of being recognized in turn by a labeled reagent, more particularly in the case where the antibody used is not labeled.

The bringing of the biological sample in the method in accordance with the invention into contact with anti-Tat antibodies may be carried out with an anti-Tat serum.

The expression <<biological sample>> is understood to mean any liquid, cell or tissue sample collected from a patient and likely to contain the antigen capable of producing an antigen-antibody complex in the presence of the appropriate antibody or antibodies. Preferably, this biological sample is blood.

Finally, a subject of the present invention is also a kit for the diagnosis of the HIV infection by determining the presence of the Tat protein or of part of the Tat protein in a biological sample, comprising:
reagents for the preparation of a medium suitable for the immunological reaction,
reagents allowing the detection of antigen-antibody complexes produced by the immunological reaction,
optionally, a reference biological sample (negative control) free of antigen,
optionally, a reference biological sample (positive control) containing a predetermined quantity of antigen.

According to an advantageous embodiment of the present invention, the reagents for preparing the medium suitable for the immunological reaction comprise anti-Tat antibodies capable of giving rise to antigen-antibody complexes with several Tat variants and preferably comprise anti-Tat Oyi or anti-Tat Bru cmM antibodies or a combination of the two.

FIGURES

FIG. 1: Comparison of the various Tat proteins.
The Tat proteins were divided into 6 structural groups which are mentioned in bold in FIG. 1A and underlined in FIG. 1B.
FIG. 1A: Amino acid sequences of the Tat PROTEINS
TatZ2 is obtained from an HIV-1 isolate close to the ancestral strains of the virus (Zhu et al., 1998). Tat Mal and Tat Eli are obtained from an HIV-1 strain isolated in the 80s in Central Africa in heterosexual HIV infections (Alizon et al., 1986). Tat Br comprises the sequence most widely used in the laboratory and is obtained from an HIV-1 strain isolated in France (Barre-Sinoussi et al., 1983), while Tat Jr is obtained from an American HIV-1 isolate (O'Brien et al., 1990). Tat Oyi is closely related to Tat Jr and Tat Bru but is obtained from an HIV strain identified in a healthy patient in Gabon (Huet et al., 1989).
FIG. 1B: Classification of the Tat proteins as a function of their size and of the mutations which they comprise for the MULTALIN program (Corpet, 1989).
FIG. 2: Sequence of the Tat protein of the HIV-Oyi variant (described by Huet et al., 1989)
FIG. 3: Purification of the 6 Tat variants by reversed phase high-performance liquid chromatography with C8 grafted column at 280 nm (see Materials and Methods for the experimental procedure).
For each frame, the bottom tracing represents the result of the peptide synthesis before purification, while the top tracing represents the result of the synthesis after the last purification step. Tat Bru (A), Tat Jr (B), TatZ2 (C), Tat Oyi (D), Tat Mal (E) and Tat Eli (F) were cleaved from the resin with TFA. After precipitation with butyl methyl ether, the proteins were dissolved in TFA buffer at 0.1% (bottom tracing in each frame). For each protein, the purification was carried out with 2 successive semipreparative HPLC runs on Hybar Merk C8 columns (4.5×125 mm, flow rate 0.8 ml/min) and then the pure fractions were analyzed (top tracing of each frame) and identified by mass spectrometry and by analysis of the amino acids (data not shown). In each case, it is observed that the principal HPLC peak represents the complete sequence. The peaks between 10 and 15 min represent derivatives of 50 residues while the peaks close to the principal fraction are derivatives with 1 to 15 deletions from the N-terminal end. The highly hydrophobic fractions are derivatives with a high molecular weight probably due to the incompletely unprotected side chains.

FIG. 4: Measurement of the affinity constant of the synthetic Tats for the nucleotide target TAR by electrophoresis (see the tests of electrophoretic mobility shift under Materials and Methods.

The protein concentration (ng/μl) is indicated at the top of each gel band. The free or complexed RNA is identified by f (for free) and c respectively. The same RNA preparation is used for the titration with the 6 proteins. A Tat Bru derivative with carboxymethylated cysteines (Bru CmC) was also tested. The dissociation constants at equilibrium (Kd) were measured directly from electrophoretic mobility shift tests. The Kd values vary approximately from 50 nM for Tat Eli and Tat Mal to about 140 nM for Tat Oyi and Tat Jr. Furthermore, the inventors have noted that in addition to the variation in the Kd values, the binding profiles with the various proteins are somewhat different. For example, low concentrations of Tat Bru produce a single well-resolved complex and it is only with rather higher concentrations (>4.5 ng/μl) that aggregates form and cannot penetrate into the acrylamide gels. By contrast, multimeric complexes are easily identified with Tat Eli even at low concentrations. It is possible to observe up to 3 retarded bands with Tat Eli and to a lesser degree with Tat Jr. Such effects are not observed with shorter proteins such as Tat Bru and Tat Mal for example, and with Tat Oyi which is a longer protein.

Figure 5:
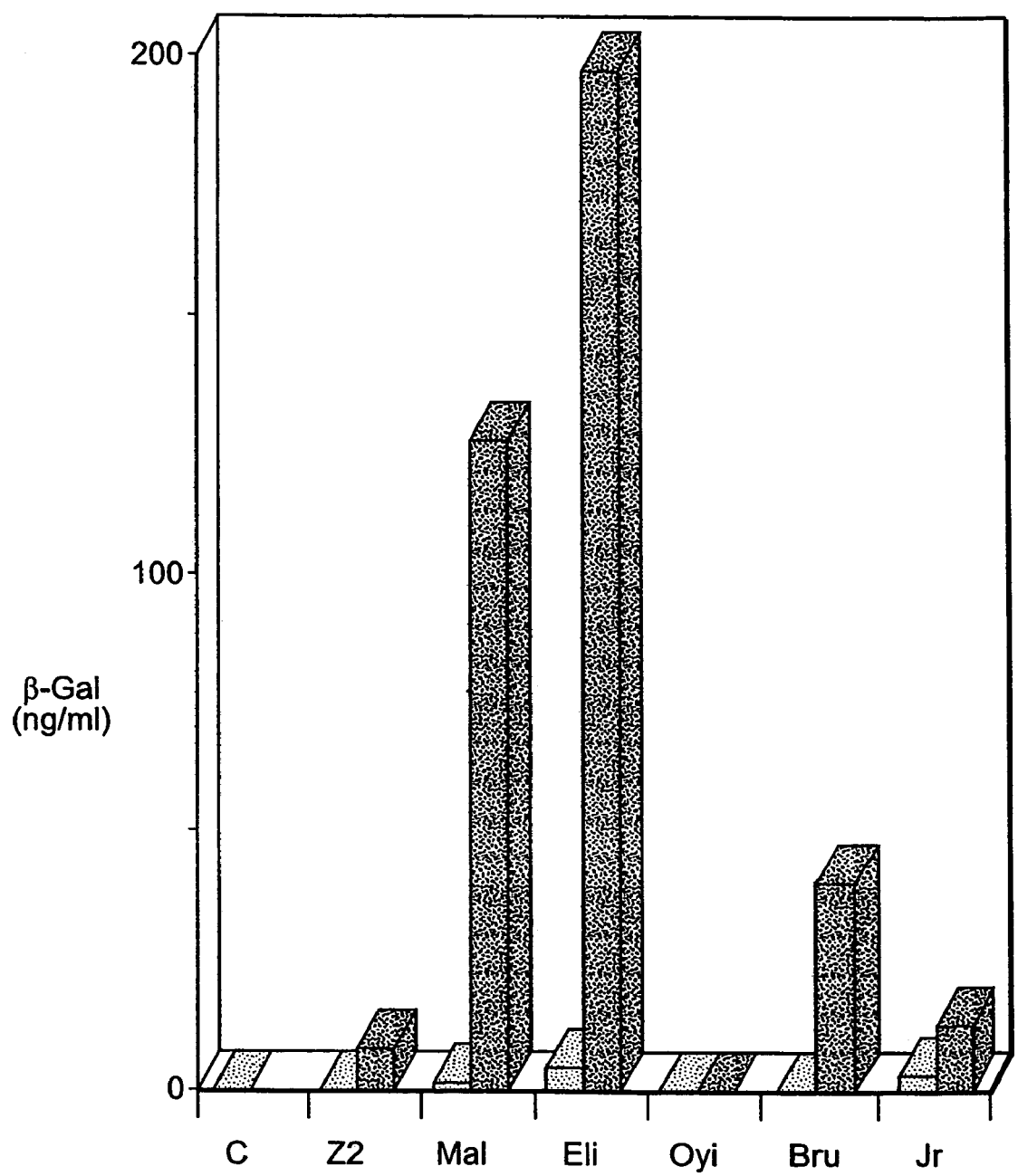

FIG. 5: Test of transactivation of the synthetic Tat proteins on HeLa cells. These cells are transfected with the HIV-1 LTR with which a LacZ reporter gene is associated. The level of β-gal protein produced is proportional to the transactivation capacity of the various synthetic Tats. The LTR contains the DNA sequences downstream and upstream which are required for the transcription of HIV and TAR is present at the beginning of the mRNA (Claven and Charneau, 1994). The cellular cofactors required for the transactivation of HIV are present in the HeLa cells. Without Tat, there is a basal expression of β-gal which is indicated as a control (C). The next histogram shows the transactivation observed with the different Tat variants using 2 concentrations: 1 μM (light gray box) and 5 μM (dark gray box). In each case, Tat is added to the cellular buffer and therefore a higher expression of β-gal than the control means that the synthetic Tat is capable of crossing the nuclear and cytoplasmic membranes, of binding to TAR and of interacting with cellular cofactors. Only Tat Bru cmC (data not shown) and Tat Oyi are deficient in this experiment whereas they bind to TAR (FIG. 1). Tat Mal and Tat Eli show a level of transactivation 3 to 4 times higher than that of Tat Bru. Tat Z2, the closest of the ancestral Tat proteins, exhibits a low level of transactivation and evolution could favor the HIV-1 isolates with a more effective Tat. Similar results have been obtained with other transfection tests using luciferase as the reporter gene and Tat Mal and Tat Eli at 1 μM indeed transactivated the LTR at a comparable level to that obtained with a transactivated Tat-pCMV (data not shown). The range of concentrations used in the various experiments extends from 0.1 μM to 10 μM (data not shown). At 0.1 μM, only Tat Eli shows a significantly higher transactivation level at the basal level. At 10 μM, the 6 Tats show such high transactivation levels that it is impossible to observe differences between them because of the saturation.

Figure 6:
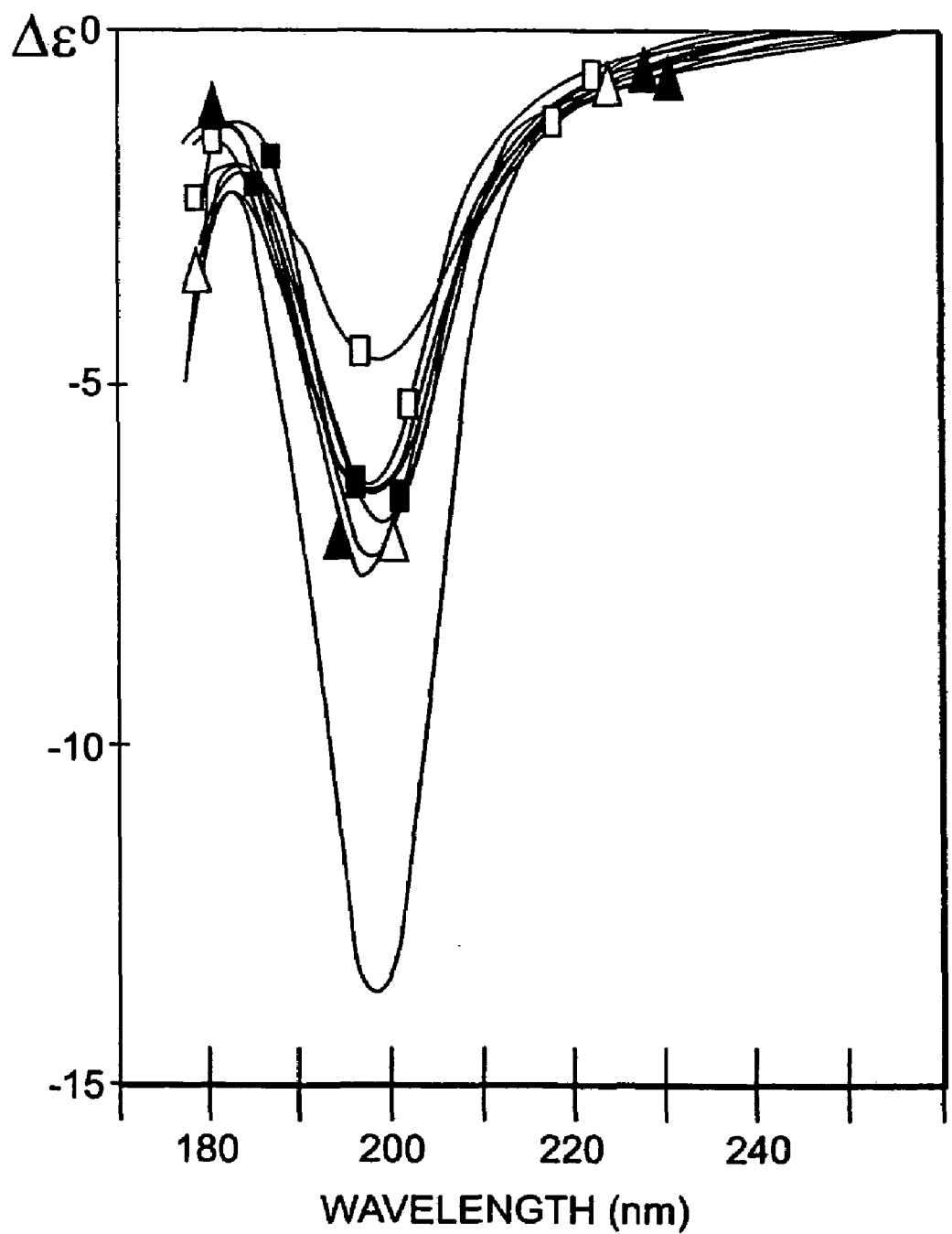

FIG. 6: Dichroic spectra of the Tat Z2 (white triangle), Tat Oyi (black triangle), Tat Bru (white circle), Tat Bru cmC (no symbol), Tat Jr (black circle), Tat Mal (white square) and Tat Eli (black square) variants.

The spectra are measured in phosphate buffer at 20 mM pH 4.5; they are recorded from 260 to 178 nm with an optical path length of 50 μm. The differences observed in the CD spectra reveal a structural heterogeneity between the Tat variants regardless of their size. It is not possible to assemble the CD spectra into 2 categories consisting of short Tats (white symbols) and long Tats (black symbols). The CD spectra are characterized by a negative band close to 200 nm typical of the unorganized structures. The intense magnitude of the band of 200 nm observed with Tat Bru cmC shows that the modification of the cysteines has caused major conformational changes compared with the other Tats.

Figure 7:
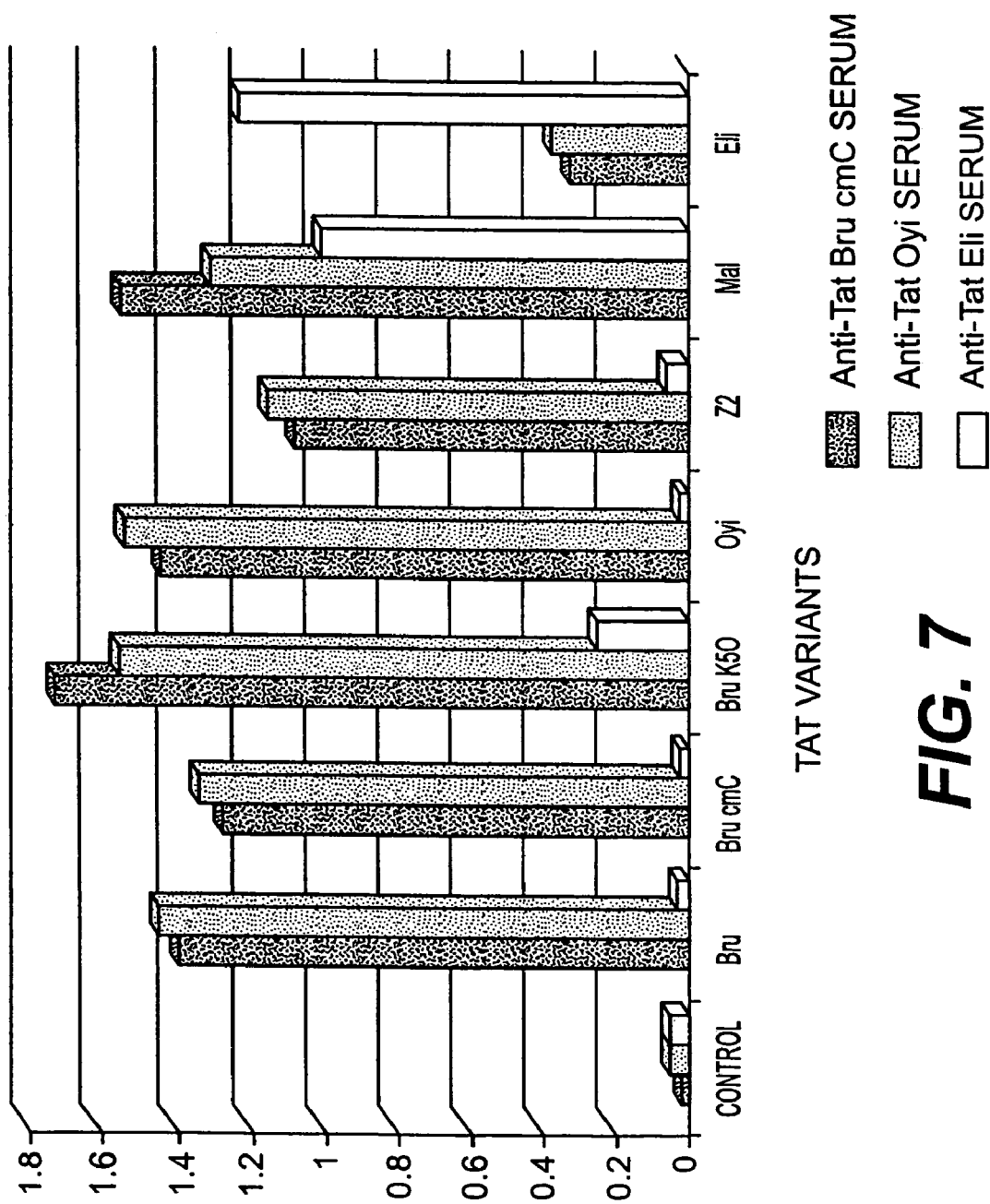

FIG. 7: Elisa tests carried out with three rabbit polyclonal sera (anti-Tat Bru cmC, anti-Tat Oyi and anti-Tat Eli) with respect to 7 variants of the Tat protein under denaturing conditions.

Figure 8A:
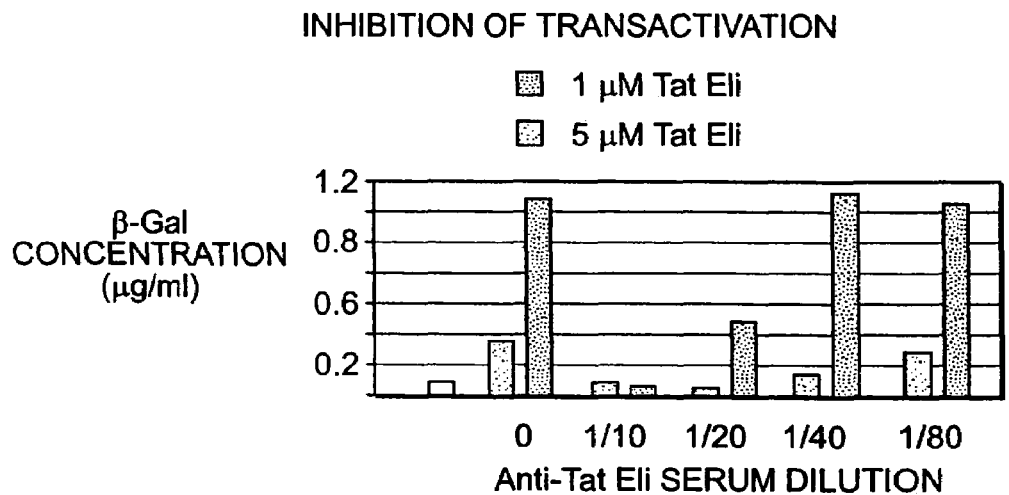
Figure 8B:
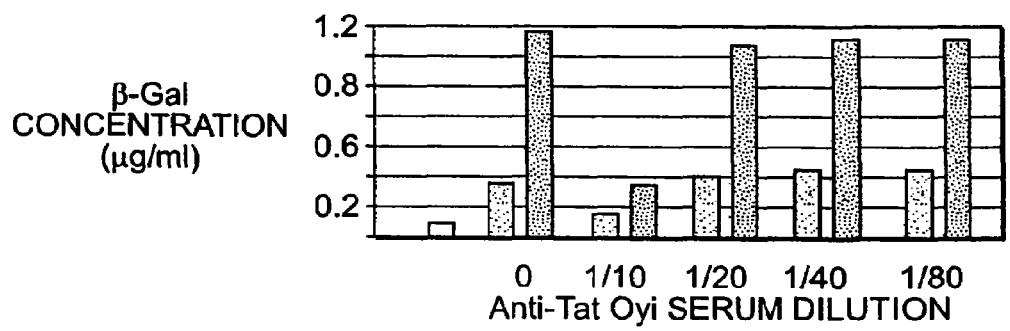
Figure 8C:
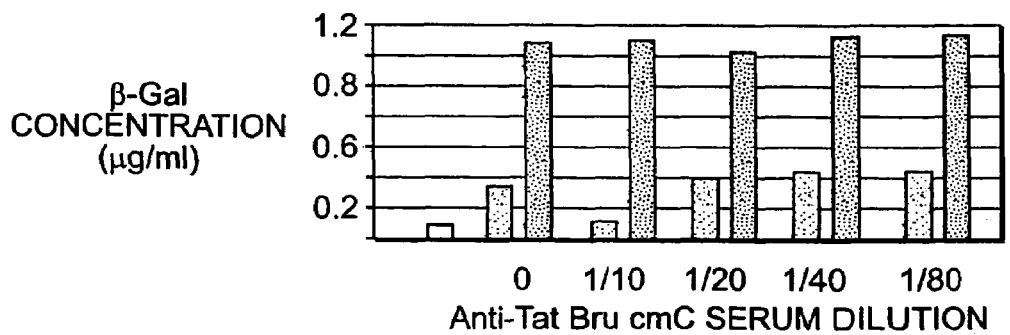

FIG. 8: Inhibition of the transactivation by Tat Eli with the anti-Tat Eli, anti-Tat Oyi and anti-Tat Bru cmC sera.

The present invention is not limited to the above description. It will be understood more clearly in the light of the examples which are only mentioned by way of illustration.

EXAMPLES

1) Materials and Methods Corresponding to FIGS. 3 to 6

Protein Synthesis, Purification and Characterization

Peptides were assembled according to the Barany and Merrifield method (1980) on a resin precharged with 4-hydroxymethyl-phenoxymethyl-copolystyrene divinylbenzene at 1% (HMP) (0.5–0.65 mmol) (Perkin Elmer, Applied Biosystem Inc., Forster City, Calif.) on an automated synthesizer (ABI 433A, Perkin Elmer, Applied Biosystem Inc., Forster City, Calif.). To avoid obtaining derivatives exhibiting deletions, the N-terminal ends without Fmoc were protected with an acetyl group after treatment with a mixture comprising 4.75% of acetic anhydride (Merck), 6.25% of DIEA at 2.0 M, 1.5% of 1-hydroxybenzotriazole 1M (HOBt) (Perkin Elmer, Applied Biosystem Inc., Warrington, GB) and 87.5% of N-methylpyrrolidone (Perkin Elmer, Forster City, Calif.). Each deprotection step was controlled with a conductivity device. The peptides were deprotected and removed from the resin with trifluoroacetic acid (TFA) supplemented with 10% methyl phenyl sulfide (Merck) and 5% of ethane dithiol (Merck). The purification was carried out with a Beckman high-performance liquid chromatography (HPLC) apparatus and a Merck C8 reversed phase column (10×250 mm). Buffer A consisted of water with 0.1% of TFA and buffer B consisted of acetonitrile with 0.1% of TFA. The gradient consisted of 20 to 40% of buffer B over 40 minutes and a flow rate of 2 ml/min. An electrospray mass spectrometry was carried out with a Perkin Elmer PE-SCIEX API 150ex simple quad. Analysis of amino acids were carried out on a Beckman, model 6300, analyzer.

Electrophoretic Mobility Shift Tests

The 59 nucleotides of the TAR RNA containing the essential pyrimidine UUU bulge was prepared in vitro by transcription with RNA polymerase T3. The binding reaction mixtures (20 μl) contained 0.2 nmol of radiolabeled TAR RNA, 0–100 ng of Tat in TK buffer (50 mM Tris pH 7.4, 20 mM KCl, 0.1% of Triton X-100). The complexes were separated from the unbound RNA by electrophoresis on 8% denaturing polyacrylamide gels containing 0.1% of Triton X-100. The gel was pre-run for 30 min before loading the sample (25 μl). The electrophoresis is continued for 90 min at about 200 V. The relative quantities of free and/or bound RNA were determined by phosphorus imaging.

Circular Dichroism (CD)

The circular dichroism spectra were measured with an optical path length of 50 μm from 260 to 178 nm on a Jobin-Yvon CD UV spectrophotometer (Long-Jumeau, FRANCE) (Mark VI). The instrument was calibrated with (+)-10-camphorsulfonic acid. A ratio of 2.1 was found between the positive CD band at 290.5 nm and the negative band at 192.5 nm. The data were collected at an interval of 0.5 nm with a scanning rate of 1 nm per minute. The CD spectra were plotted in the form of Δεper amide. The samples were prepared in a phosphate buffer at 20 mM (pH 4.5). The protein concentrations were in a range of 0.5 to 1 mg/ml.

Transactivation with Cells Transfected with HIV LTR

The functional transactivation by a synthetic Tat was determined using P4 cells. These CD4-HeLa cells carry the bacterial lacZ gene under the control of HIV LTR and the cytoplasmic accumulation of β-galactosidase was strictly dependent on the presence of Tat. 80% of the confluent cells plated on a 12-well plate were incubated for 24 h at 37° C., in the presence of 5% $CO_2$, with the Tat protein contained in a DMEM medium supplemented with 0.1% BSA. Following this period of incubation, the cells were washed with phosphate-buffered saline and the proteins were extracted and analyzed for β-galactosidase with a commercial immunoabsorption test using an enzyme linked to an antigen (ELISA) for β-galactosidase, Boehringer Mannheim, FRANCE), according to the manufacturer's instructions. The values were normalized using the concentration of the total proteins of the different cell lysates as determined by the Bradford method.

Inhibition of Transactivation

The above experiments of transactivation with cells transfected with HIV LTR were reproduced, but this time with addition to the culture medium either of an anti-Tat Eli serum, or of an anti-Tat Oyi serum, or of an anti-Tat Bru serum. The Tat protein was, for its part, obtained from Eli variants.

When compared with control medium that does not contain antibodies, inactivation of the transactivation of the Tat Eli protein by anti-Tat Ovi antibodies has been observed.

2) Materials and Methods Corresponding to FIG. 7

The immunization conditions are an intradermal injection of 100 μg of purified Tat protein in 0.5 ml of 100 mM phosphate buffer pH 4.5 plus 0.5 ml of complete Freund's adjuvant (Day 0). A first booster is performed on D21 under the same conditions but with incomplete Freund's adjuvant (0.5 ml). A second booster is performed on D42 identical to D41. Blood is collected on D53 in FST tubes and the serum is obtained after centrifugation at 2000 revolutions/min. The dilution of the sera is 1/1000.

Elisa: The test is performed on a Maxisorp U96 plate (Polylabo). The proteins in phosphate buffer pH 4.5 are incubated on the plate overnight at 4° C. After saturation in MPBS buffer (8 g/l NaCl, 0.2 g/l KCl, 1.44 g/l $Na_2HPO_4$, 0.24 g/l $KH_2PO_4$, 5% skimmed milk adjusted to pH 7.4 with HCl), the proteins are incubated with rabbit primary antibody for 1 hour. Then incubation with a goat antibody coupled to peroxidase specific for the rabbit Fc fragment (Cappel) for one hour. The revealing is carried out in the presence of $H_2O_2$, 100 mM citric acid, 50 mM NaOH and 0.2 mg/ml ABTS (Boehringer). The absorbance is read at 405 nm.

Without dilution, the anti-Tat Eli serum is capable of recognizing all the Tat variants or derivatives.

3) Materials and Methods for the Western Blotting

Western blotting: The proteins are first denatured in the presence of 3 M Tris-HCl, pH 8.8, 5% β-mercaptoethanol, 2% SDS, 10% glycerol, and bromophenol blue. They are separated by electrophoresis on 15% polyacrylamide gel. The proteins are then transferred onto nitrocellulose membranes so as to be revealed by immunodetection. The specific sites are blocked with a PBS solution (8 g/l NaCl, 0.2 g/l KCl, 1.44 g/l $Na_2HPO_4$, 0.24 g/l $KH_2PO_4$, adjusted to pH 7.4 with HCl) containing 5% skimmed milk. The nitrocellulose membrane is incubated with rabbit primary antibody for one hour. Then incubation with a goat antibody coupled to peroxidase specific for the rabbit Fc fragment (Sigma). The revealing is carried out in the presence of $H_2CO_2$, PBS and diaminobenzamidine. (Photograph of the gel not shown in the present invention).

4) Materials and Methods Corresponding to FIG. 8

The transactivation is measured with human HeLa cells transfected with HIV-1 LTR and a reporter gene for the β-galactosidase protein (LacZ) according to the protocol described for FIG. 5.

The sera are obtained in rabbits according to the protocol described for FIG. 7.

100 μl of three anti-Tat sera, namely anti-Tat Eli, anti-Tat Oyi and anti-Tat Bru cmC in increasing dilutions, are added to a cell culture medium, followed by 100 μl of the Tat Eli variant at 1 or 5 μM. The cytoplasmic accumulation of β-galactosidase therefore depends on the presence of Tat.

First of all, it is observed, at equivalent dilution, that the anti-Tat Eli serum is the most effective. This is logical because the serum contains antibodies produced against the same variant as that whose transactivation activity it is sought to neutralize. However, it should be emphasized that Tat Oyi is capable of generating antibodies which significantly neutralize the transactivation activity of Tat Eli. This inhibition is in fact greater than that observed in particular for the 1/10 dilution using the anti-Tat Bru cmC serum. This confirms the benefit of the anti-Tat Oyi antibodies against other Tat variants.

REFERENCES

Alizon, M., Wain-Hobson, S., Montagnier, L., & Sonigo, P. (1986) *Cell* 46, 63–74

Barany, G. & Merrifield, R. B. (1980) in Gross, E., & Meinhofer, J. (Eds) *The peptide: Analysis, Synthesis, Biology*. Academic Press, New York, Vol. 2, pp 1–284

Barre-Sinoussi, F., Chermann, J. C., Rey, F., Nugeyre, M. T., Chamaret, S., Gruest, J., Dauguet, C., Axler-Blin, C., Vezinet-Brun, F., Rouzioux, C., Rozenbaum, W. & Montagnier, L. (1983) *Science* 220, 868–871

Clavel, F. & Charneau, P. (1994) *J. Virol* 68, 1179–1185

Corpet, F. (1989) Nucl. Acid. Res. 22, 10881–10890.

Delaporte E., Janssens W., Peeters M., Buve A., Dibanga G., Perret J. L., Ditsambou V., Mba J. R., Courbot M. C., Georges A., Bourgeois A., Samb B., Henzel D., Heyndrickx L., Fransen K., van der Groen G., Larouze B. (1996) *AIDS* 8, 903–910

Grégoire, C. & Loret, E. P. 1996. *J. Biol. Chem.* 271, 22641–22646

Huet, T., Dazza, M. C., Brun-Vezinet, F., Roelants, G. E. & Wain-Hobson, S. 1989 *AIDS* 3, 707–715

Jeang, K. T. (1996) in Los Alamos National Laboratory (Ed) *HIV-1 Tat: Structure & Function* Human Retroviruses & AIDS compendium. III, pp 3–18

Jeang, K. T., Xiao, H., & Rich, E. A. (1999) *J. Biol. Chem.* 274, 28837–28840.

Le Buanec, H., Lachgar, A., Bizzini, B., Zagury, J. F., Rappaport, J., Santagostino, E., Muca-Perja, M. & Gringeri, A. 1998. *Biomed. Pharmacother* 10, 431–435

O'Brien, W. A., Koyanagi, Y., Namazie, A., Zhao, J. Q., Diagne, A., Idler, K., Zack, J. A. & Chen, I. S. (1990) *Nature* 348, 69–73

Westendorp, M. O., Frank, R., Ochsenbauer, C., Stricker, K., Dhein, J., Walczak, H., Debatin, K. M. & Krammer, P. H. 1995 *Nature* 375, 497–500

Zhu, T., Korber, B. T., Nahmias, A. J., Hooper, E., Sharp, P. M. & Ho, D. D. (1998) *Nature* 391, 594–597

---

The invention claimed is:

1. A method for detecting the presence of any variant of Tat protein other than TatOyi protein in a biological sample, comprising:

bringing said sample into contact with anti-TatOyi antibodies under nondenaturing conditions, detecting the presence of the Tat protein by determining the presence of the antigen-antibody complexes comprising any variant of Tat protein other than TatOyi.

2. A kit for the diagnosis of infection by any variant of HIV-1, other than HIV-1 Oyi variant, wherein the kit determines the presence of any variant of Tat protein other than TatOyi in a biological sample and comprises:

anti-TatOyi antibodies, reagents for the preparation of a medium suitable for the antigen-antibody reaction, optionally, a reference biological sample (negative control) free of antigen, optionally, a reference biological sample (positive control) containing a predetermined quantity of antigen wherein the positive control is any variant of Tat protein other than Tat Oyi.

* * * * *

SEQUENCE LISTING

<160> NUMBER OF SEQ ID NOS: 20

<210> SEQ ID NO 1
<211> LENGTH: 86
<212> TYPE: PRT
<213> ORGANISM: Human immunodeficiency virus-1

<400> SEQUENCE: 1

```
Met Asp Pro Val Asp Pro Asn Ile Glu Pro Trp Asn His Pro Gly Ser
 1               5                  10                  15

Gln Pro Lys Thr Ala Cys Asn Arg Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asp
65                  70                  75                  80

Pro Thr Gly Pro Lys Glu
                85
```

<210> SEQ ID NO 2
<211> LENGTH: 86
<212> TYPE: PRT
<213> ORGANISM: Human immunodeficiency virus-1

<400> SEQUENCE: 2

```
Met Asp Pro Val Asp Pro Asn Leu Glu Pro Trp Asn His Pro Gly Ser
 1               5                  10                  15

Gln Pro Lys Thr Ala Cys Asn Arg Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Pro Ser Gln Gly Gly Gln Thr
    50                  55                  60

His Gln Asp Pro Ile Pro Lys Gln Pro Ser Ser Gln Pro Arg Gly Asn
65                  70                  75                  80

Pro Thr Gly Pro Lys Glu
                85
```

<210> SEQ ID NO 3
<211> LENGTH: 86
<212> TYPE: PRT
<213> ORGANISM: Human immunodeficiency virus-1

-continued

```
<400> SEQUENCE: 3

Met Asp Pro Val Asp Pro Asn Leu Glu Ser Trp Asn His Pro Gly Ser
1               5                   10                  15

Gln Pro Arg Thr Ala Cys Asn Lys Cys His Cys Lys Lys Cys Cys Tyr
            20                  25                  30

His Cys Gln Val Cys Phe Ile Thr Lys Gly Leu Gly Ile Ser Tyr Gly
        35                  40                  45

Arg Lys Lys Arg Arg Gln Arg Arg Lys Pro Pro Gln Gly Asp Gln Ala
    50                  55                  60

His Gln Val Pro Ile Pro Glu Gln Pro Ser Ser Gln Ser Arg Gly Asp
65                  70                  75                  80

Pro Thr Gly Pro Lys Lys
                85

<210> SEQ ID NO 4
<211> LENGTH: 87
<212> TYPE: PRT
<213> ORGANISM: Human immunodeficiency virus-1

<400> SEQUENCE: 4

Met Asp Pro Val Asp Pro Asn Leu Glu Pro Trp Asn His Pro Gly Ser
1               5                   10                  15

Gln Pro Arg Thr Pro Cys Asn Lys Cys Tyr Cys Lys Lys Cys Cys Tyr
            20                  25                  30

His Cys Gln Met Cys Phe Ile Thr Lys Gly Leu Gly Ile Ser Tyr Gly
        35                  40                  45

Arg Lys Lys Arg Arg Gln Arg Arg Pro Pro Gln Gly Asn Gln Ala
    50                  55                  60

His Gln Asp Pro Leu Pro Glu Gln Pro Ser Ser Gln His Arg Gly Asp
65                  70                  75                  80

His Pro Thr Gly Pro Lys Glu
                85

<210> SEQ ID NO 5
<211> LENGTH: 86
<212> TYPE: PRT
<213> ORGANISM: Human immunodeficiency virus-1

<400> SEQUENCE: 5

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Ala His Gln Asn Ser Gln Thr
    50                  55                  60

His Gln Ala Ser Leu Ser Lys Gln Pro Thr Ser Gln Ser Arg Gly Asp
65                  70                  75                  80

Pro Thr Gly Pro Lys Glu
                85

<210> SEQ ID NO 6
<211> LENGTH: 86
<212> TYPE: PRT
<213> ORGANISM: Human immunodeficiency virus-1

<400> SEQUENCE: 6
```

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Gln Arg Arg Ala Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 7
<211> LENGTH: 86
<212> TYPE: PRT
<213> ORGANISM: Human immunodeficiency virus-1

<400> SEQUENCE: 7

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Gln Arg Arg Pro Pro Gln Gly Ser Gln Thr
    50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 8
<211> LENGTH: 86
<212> TYPE: PRT
<213> ORGANISM: Human immunodeficiency virus-1

<400> SEQUENCE: 8

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
                20                  25                  30

His Cys Gln Val Cys Phe Ile Thr Lys Ala Leu Gly Ile Ser Tyr Gly
            35                  40                  45

Arg Lys Lys Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 9
<211> LENGTH: 86
<212> TYPE: PRT
<213> ORGANISM: Human immunodeficiency virus-1

<400> SEQUENCE: 9
```

Met Glu Pro Val Asp Pro Arg Leu Glu Pro Trp Lys His Pro Gly Ser
1               5                   10                  15

Gln Pro Lys Thr Ala Cys Thr Thr Cys Tyr Cys Lys Lys Cys Cys Phe
                20                  25                  30

His Cys Gln Val Cys Phe Thr Thr Lys Ala Leu Gly Ile Ser Tyr Gly
            35                  40                  45

Arg Lys Lys Arg Arg Gln Arg Arg Pro Pro Gln Gly Ser Gln Thr
        50                  55                  60

His Gln Val Ser Leu Ser Lys Gln Pro Thr Ser Gln Pro Arg Gly Asp
65                  70                  75                  80

Pro Thr Gly Pro Lys Glu
                85

<210> SEQ ID NO 10
<211> LENGTH: 101
<212> TYPE: PRT
<213> ORGANISM: Human immunodeficiency virus-1

<400> SEQUENCE: 10

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
                20                  25                  30

His Cys Gln Val Cys Phe Thr Lys Lys Gly Leu Gly Ile Ser Tyr Gly
            35                  40                  45

Arg Lys Lys Arg Arg Gln Arg Arg Pro Pro Gln Asp Ser Gln Thr
        50                  55                  60

His Gln Ser Ser Leu Ser Lys Gln Pro Thr Ser Gln Leu Arg Gly Asp
65                  70                  75                  80

Pro Thr Gly Pro Thr Glu Ser Lys Lys Lys Val Glu Arg Glu Thr Glu
                85                  90                  95

Thr Asp Pro Val His
                100

<210> SEQ ID NO 11
<211> LENGTH: 101
<212> TYPE: PRT
<213> ORGANISM: Human immunodeficiency virus-1

<400> SEQUENCE: 11

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
                20                  25                  30

His Cys Tyr Ala Cys Phe Thr Arg Lys Gly Leu Gly Ile Ser Tyr Gly
            35                  40                  45

Arg Lys Lys Arg Arg Gln Arg Arg Ala Pro Gln Asp Ser Gln Thr
        50                  55                  60

His Gln Ala Ser Leu Ser Lys Gln Pro Ala Ser Gln Ser Arg Gly Asp
65                  70                  75                  80

Pro Thr Gly Pro Thr Glu Ser Lys Lys Lys Val Glu Arg Glu Thr Glu
                85                  90                  95

Thr Asp Pro Phe Asp
                100

<210> SEQ ID NO 12
<211> LENGTH: 101

```
<212> TYPE: PRT
<213> ORGANISM: Human immunodeficiency virus-1

<400> SEQUENCE: 12

Met Asp Pro Val Asp Pro Arg Leu Glu Pro Trp Lys His Pro Gly Ser
 1               5                  10                  15

Gln Pro Lys Ala Ala Cys Thr Ser Cys Tyr Cys Lys Lys Cys Cys Phe
                20                  25                  30

His Cys Gln Val Cys Phe Thr Thr Lys Gly Leu Gly Ile Ser Tyr Gly
            35                  40                  45

Arg Lys Lys Arg Arg Gln Arg Arg Ala Pro Gln Asp Ser Gln Thr
50                      55                  60

His Gln Val Ser Leu Pro Lys Gln Pro Ala Ser Gln Ala Arg Gly Asp
65                  70                  75                  80

Pro Thr Gly Pro Lys Glu Ser Lys Lys Val Glu Arg Glu Thr Glu
                85                  90                  95

Thr Asp Pro Val Asp
            100

<210> SEQ ID NO 13
<211> LENGTH: 101
<212> TYPE: PRT
<213> ORGANISM: Human immunodeficiency virus-1

<400> SEQUENCE: 13

Met Glu Pro Val Asp Pro Ser Leu Glu Pro Trp Lys His Pro Gly Ser
 1               5                  10                  15

Gln Pro Lys Thr Ala Cys Thr Asn Cys Tyr Cys Lys Lys Cys Cys Leu
                20                  25                  30

His Cys Gln Val Cys Phe Thr Thr Lys Gly Leu Gly Ile Ser Tyr Gly
            35                  40                  45

Arg Lys Lys Arg Arg Gln Arg Arg Pro Pro Gln Asp Ser Gln Thr
50                      55                  60

His Gln Val Ser Leu Pro Lys Gln Pro Ser Ser Gln Gln Arg Gly Asp
65                  70                  75                  80

Pro Thr Gly Pro Lys Glu Ser Lys Lys Val Glu Arg Glu Thr Glu
                85                  90                  95

Thr Asp Pro Asp Asn
            100

<210> SEQ ID NO 14
<211> LENGTH: 101
<212> TYPE: PRT
<213> ORGANISM: Human immunodeficiency virus-1

<400> SEQUENCE: 14

Met Glu Pro Val Asp Pro Arg Leu Glu Pro Trp Lys His Pro Gly Ser
 1               5                  10                  15

Gln Pro Lys Thr Ala Cys Thr Thr Cys Tyr Cys Lys Lys Cys Cys Phe
                20                  25                  30

His Cys Gln Val Cys Phe Thr Lys Lys Ala Leu Gly Ile Ser Tyr Gly
            35                  40                  45

Arg Lys Lys Arg Arg Gln Arg Arg Ala Pro Glu Asp Ser Gln Thr
50                      55                  60

His Gln Val Ser Leu Pro Lys Gln Pro Ala Pro Gln Phe Arg Gly Asp
65                  70                  75                  80

Pro Thr Gly Pro Lys Glu Ser Lys Lys Lys Val Glu Arg Glu Thr Glu
```

Thr His Pro Val Asp
            100

<210> SEQ ID NO 15
<211> LENGTH: 101
<212> TYPE: PRT
<213> ORGANISM: Human immunodeficiency virus-1

<400> SEQUENCE: 15

Met Glu Pro Val Asp Pro Arg Leu Glu Pro Trp Lys His Pro Gly Ser
  1               5                  10                  15

Gln Pro Lys Thr Ala Cys Thr Asn Cys Tyr Cys Lys Lys Cys Cys Phe
             20                  25                  30

His Cys Gln Val Cys Phe Thr Lys Lys Ala Leu Gly Ile Ser Tyr Gly
         35                  40                  45

Arg Lys Lys Arg Arg Gln Arg Arg Ala His Gln Asp Ser Gln Asn
     50                  55                  60

His Gln Ala Ser Leu Ser Lys Gln Pro Ser Ser Gln Thr Arg Gly Asp
 65                  70                  75                  80

Pro Thr Gly Pro Lys Glu Pro Lys Lys Glu Val Glu Arg Glu Ala Glu
                 85                  90                  95

Thr Asp Pro Leu Asp
            100

<210> SEQ ID NO 16
<211> LENGTH: 100
<212> TYPE: PRT
<213> ORGANISM: Human immunodeficiency virus-1

<400> SEQUENCE: 16

Met Glu Pro Val Asp Pro Arg Leu Glu Pro Trp Lys His Pro Gly Ser
  1               5                  10                  15

Gln Pro Lys Thr Ala Cys Thr Asn Cys Tyr Cys Lys Lys Cys Cys Phe
             20                  25                  30

His Cys Gln Val Cys Phe Ile Thr Gly Leu Gly Ile Ser Tyr Gly Arg
         35                  40                  45

Lys Lys Arg Arg Gln Arg Arg Arg Ala Pro Pro Asp Ser Glu Val His
 50                  55                  60

Gln Val Ser Leu Pro Lys Gln Pro Ala Ser Gln Pro Gln Gly Asp Pro
 65                  70                  75                  80

Thr Gly Pro Lys Glu Ser Lys Lys Lys Val Glu Arg Glu Thr Glu Thr
                 85                  90                  95

Asp Pro Val His
            100

<210> SEQ ID NO 17
<211> LENGTH: 101
<212> TYPE: PRT
<213> ORGANISM: Human immunodeficiency virus-1

<400> SEQUENCE: 17

Met Glu Pro Val Asp Pro Arg Leu Glu Pro Trp Lys His Pro Gly Ser
  1               5                  10                  15

Gln Pro Lys Thr Ala Ser Asn Asn Cys Tyr Cys Lys Arg Cys Cys Leu
             20                  25                  30

His Cys Gln Val Cys Phe Thr Lys Lys Gly Leu Gly Ile Ser Tyr Gly
         35                  40                  45

```
Arg Lys Lys Arg Arg Gln Arg Arg Ala Pro Gln Asp Ser Lys Thr
    50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Lys Val Glu Arg Glu Thr Glu
                85                  90                  95

Thr Asp Pro Glu Asp
            100

<210> SEQ ID NO 18
<211> LENGTH: 102
<212> TYPE: PRT
<213> ORGANISM: Human immunodeficiency virus-1

<400> SEQUENCE: 18

Met Glu Pro Val Asp Pro Arg Leu Glu Pro Trp Lys His Pro Gly Ser
  1               5                  10                  15

Gln Pro Lys Thr Ala Cys Asn Asn Cys Tyr Cys Lys Cys Cys Tyr
                20                  25                  30

His Cys Gln Val Cys Phe Leu Lys Gly Leu Gly Ile Ser Tyr Gly Arg
            35                  40                  45

Lys Lys Arg Arg Gln Arg Arg Gly Pro Pro Gln Gly Ser Gln Thr
    50                  55                  60

His Gln Val Ser Leu Ser Lys Gln Pro Thr Ser Gln Pro Arg Gly Asp
 65                  70                  75                  80

Pro Thr Gly Pro Lys Glu Ser Lys Glu Lys Val Glu Arg Glu Thr Glu
                85                  90                  95

Thr Asp Pro Ala Val Gln
            100

<210> SEQ ID NO 19
<211> LENGTH: 99
<212> TYPE: PRT
<213> ORGANISM: Human immunodeficiency virus-1

<400> SEQUENCE: 19

Met Asp Pro Val Asp Pro Asn Leu Glu Pro Trp Asn His Pro Gly Ser
  1               5                  10                  15

Gln Pro Arg Thr Pro Cys Asn Lys Cys His Cys Lys Lys Cys Cys Tyr
                20                  25                  30

His Cys Pro Val Cys Phe Ile Leu Asn Lys Gly Leu Gly Ile Ser Tyr
            35                  40                  45

Gly Arg Lys Lys Arg Arg Gln Arg Arg Gly Pro Gln Gly Gln Gln Ala
    50                  55                  60

His Gln Val Pro Ile Pro Lys Gln Pro Ser Ser Gln Pro Arg Gly Asp
 65                  70                  75                  80

Pro Thr Gly Pro Lys Glu Gln Lys Lys Val Glu Ser Glu Ala Glu
                85                  90                  95

Thr Asp Pro

<210> SEQ ID NO 20
<211> LENGTH: 101
<212> TYPE: PRT
<213> ORGANISM: Human immunodeficiency virus-1

<400> SEQUENCE: 20

Met Glu Pro Val Asp Pro Arg Leu Glu Pro Trp Lys His Pro Gly Ser
```

-continued

```
  1               5                   10                  15

Gln Pro Lys Thr Ala Ser Asn Asn Cys Tyr Cys Lys Arg Cys Cys Leu
            20                  25                  30

His Cys Gln Val Cys Phe Thr Lys Lys Gly Leu Gly Ile Ser Tyr Gly
        35                  40                  45

Arg Lys Lys Arg Arg Gln Arg Arg Arg Ala Pro Gln Asp Ser Lys Thr
    50                  55                  60

His Gln Val Ser Leu Ser Lys Gln Pro Ala Ser Gln Pro Arg Gly Asp
 65                  70                  75                  80

Pro Thr Gly Pro Lys Glu Ser Lys Lys Lys Val Glu Arg Glu Thr Glu
                85                  90                  95

Thr Asp Pro Glu Asp
            100
```